US011971380B2

(12) United States Patent
Eriksen et al.

(10) Patent No.: US 11,971,380 B2
(45) Date of Patent: Apr. 30, 2024

(54) PUMP DEVICE AND METHOD FOR DETERMINING THE CONCENTRATION OF A SUBSTANCE INSIDE A LIQUID (71) Applicant: GRUNDFOS HOLDING A/S, Bjerringbro (DK)

(72) Inventors: Gert Friis Eriksen, Bjerringbro (DK); Jørgen Jensen, Langa (DK)

(73) Assignee: GRUNDFOS HOLDING A/S, Bjerringbro (DK)

( * ) Notice: Subject to any disclaimer, the term of this patent is extended or adjusted under 35 U.S.C. 154(b) by 307 days.

(21) Appl. No.: 17/434,339

(22) PCT Filed: Feb. 26, 2020

(86) PCT No.: PCT/EP2020/054986
§ 371 (c)(1),
(2) Date: Aug. 26, 2021

(87) PCT Pub. No.: WO2020/173890
PCT Pub. Date: Sep. 3, 2020

(65) Prior Publication Data
US 2022/0057351 A1    Feb. 24, 2022

(30) Foreign Application Priority Data

Feb. 27, 2019 (EP) ..................... 19159680

(51) Int. Cl.
*G01N 27/02* (2006.01)
*F04D 13/06* (2006.01)
(Continued)

(52) U.S. Cl.
CPC .......... *G01N 27/026* (2013.01); *F04D 13/06* (2013.01); *F04D 15/0077* (2013.01);
(Continued)

(58) Field of Classification Search
None
See application file for complete search history.

(56) References Cited

U.S. PATENT DOCUMENTS 6,511,851 B1 * 1/2003 Payne .................... G01N 33/14
436/151
2005/0104607 A1 * 5/2005 Byington ........... G01N 33/2888
324/693
(Continued)

FOREIGN PATENT DOCUMENTS

EP    1617212 A1    1/2006
EP    2775297 A1    9/2014
EP    2890869 B1    1/2019

*Primary Examiner* — Jermele M Hollington
*Assistant Examiner* — Suresh K Rajaputra
(74) *Attorney, Agent, or Firm* — McGlew and Tuttle, P.C.

(57) ABSTRACT

A pump device has at least one chamber (22) or conduit containing or provided for containing a liquid, a concentration sensor (24) arranged in the chamber (22) or conduit for detecting a concentration of a substance in the liquid and an evaluation unit (28) connected to the sensor (24). The sensor (24) and the evaluation unit (28) are configured for an electrical impedance measurement. The evaluation unit (28) is configured such that a measurement for detecting the concentration is carried out by use of an electrical signal applied to the sensor (24) having at least one frequency corresponding to or above an upper cut-off frequency ($f_2$) of a frequency range showing a constant electrical impedance ($R_m$). A method is provided for determining the concentration of a substance inside a liquid.

21 Claims, 3 Drawing Sheets (51) Int. Cl.
 *F04D 15/00* (2006.01)
 *F04D 15/02* (2006.01)
 *G01N 33/08* (2006.01)
 *G01N 33/28* (2006.01)

(52) U.S. Cl.
 CPC ..... *F04D 15/0088* (2013.01); *F04D 15/0263* (2013.01); *G01N 33/2847* (2013.01)

(56) References Cited

U.S. PATENT DOCUMENTS

| | | | | |
|---|---|---|---|---|
| 2012/0287431 | A1* | 11/2012 | Matsiev | G01N 27/026 356/306 |
| 2014/0326340 | A1* | 11/2014 | Kuriki | G01N 17/02 137/565.11 |
| 2014/0352428 | A1* | 12/2014 | Kato | G01F 23/268 73/304 C |
| 2015/0233887 | A1* | 8/2015 | Surman | G01N 33/2823 73/61.61 |
| 2022/0050071 | A1* | 2/2022 | Platt | G01N 33/2835 |
| 2022/0326212 | A1* | 10/2022 | Potyrailo | B61L 3/002 |

* cited by examiner

PUMP DEVICE AND METHOD FOR DETERMINING THE CONCENTRATION OF A SUBSTANCE INSIDE A LIQUID

CROSS REFERENCE TO RELATED APPLICATIONS

This application is a United States National Phase Application of International Application PCT/EP2020/054986, filed Feb. 26, 2020, and claims the benefit of priority under 35 U.S.C. § 119 of European Application 19159680.8, filed Feb. 27, 2019, the entire contents of which are incorporated herein by reference.

TECHNICAL FIELD

The invention refers to a pump device, a method and a sensor unit for determining the concentration of a substance or compound in a liquid contained in a pump.

The invention refers to a pump device having at least one chamber or conduit containing or provided for containing a liquid. Furthermore, the invention refers to a method for determining the concentration of a substance or compound in a liquid contained in a chamber or conduit of a pump.

TECHNICAL BACKGROUND

For cooling or sealing applications in pumps, it is the problem to ensure the right properties of the coolant inside a chamber of the pump. For example, in wastewater pumps, sealing systems containing a fluid inside a chamber are used to separate the electric drive motor from the liquid to be pumped. These sealing systems comprise two shaft seals with a chamber between, which chamber is filled with a lubricant and coolant to improve the lifetime of the shaft seals. Typical lubricants/coolants are mineral oil or a glycol water mixture. Due to wear of the seals, a leakage may occur and a liquid to be pumped, for example water, may enter the chamber filled with the lubricant. To recognize such wear, it is known to place a sensor in the chamber detecting the concentration of the entering liquid. For example, a capacitive sensor to detect water entering the oil inside such a sealing chamber is known from EP 1617212 A1. This known sensor can be used to detect water in oil. However, this sensor is less suitable for systems using a glycol-water-mixture as coolant or lubricant in the sealing system, since such a mixture yields a much smaller change in capacitance than an oil-water mixture, given a similar change in concentration. Consequently, the sensitivity of these known sensors normally is insufficient for detecting concentration changes in a glycol water mixture.

EP 2775297 A1 discloses a device for detecting a change in concentration of a corrosion inhibitor to be used in a hot-water supply heating system. US 2005/0104607 A1 discloses a device for an electrochemical impedance measurement system used as a sensing system suitable for measuring the broadband impedance of oil or other fluids used in or with equipment, machinery and the like. Both prior art solutions are using a low frequency range below a lower cut-off frequency of the fluid, where the properties of the electrode will have a significant impact on the impedance measurements of the fluid properties. The systems are not suitable for the detection of the concentration of glycol.

SUMMARY

In view of this, it is an object of the invention to provide an improved pump device and an improved method for determining a concentration allowing the detection of a change of concentration of a substance inside a liquid for other types of lubricants than oil, in particular lubricants having a mixture of glycol and water.

This object is achieved by a pump device having features according to the invention, by a method having features according to the invention and a sensor unit having features according to the invention. Preferred embodiments are disclosed in the following description as well as the accompanying drawings.

The pump device according to the invention has at least one chamber or conduit, which may contain a liquid or which may be provided for containing a liquid. This chamber or circuit may for example be part of a cooling or sealing system. In particular, the chamber may be a chamber between two shaft seals of an electric drive motor of a pump. Such closed chamber may be prefilled with a lubricant or coolant, as in particular a glycol-water-mixture. However, any other lubricant, in particular a mixture of different substances forming such lubricant or coolant may be used. In an alternative solution, a conduit may be part of the flow path for the liquid to be pumped. In such a solution, the conduit is filled by the liquid to be pumped.

According to the invention, such conduit or chamber is provided with a concentration sensor arranged in said chamber or conduit, such that the sensor can detect or analyze a concentration of a substance or compound in said liquid. For this, the sensor is connected with an evaluation unit receiving and evaluating the sensor signals to monitor the concentration inside the chamber. This may be for example the concentration of glycol in water, as used in a chamber in a sealing system, as mentioned above.

According to the invention, said sensor and said evaluation unit are configured for an electrical impedance measurement. Such a measurement can be used also for detecting concentrations showing only a small change in capacitance with a change of concentration. For example, a change in concentration of glycol in water can be detected by such electrical impedance measurement.

According to the invention, said evaluation unit is configured such that a measurement for detecting said concentration is carried out by use of an electrical signal applied to said sensor. Said sensor in particular comprises at least two separate electrodes, to which said signal is applied. The signal has at least one frequency corresponding to or above an upper cut-off frequency of a frequency range showing a constant electrical impedance. To use a frequency at or above said cut-off frequency allows to detect the capacitance of the media or liquid eliminating the influence of further capacitances of the electrodes.

Furthermore, according to a preferred embodiment the sensor comprises electrodes coming into direct contact with the liquid to be analyzed. By this, the influence of an insulating material, in particular the capacitance of an insulating material, as for example glass, can be avoided. However, by such a design, the resistance of the liquid or media between the electrodes has an influence on the measurement. Furthermore, ions in the media may form a polarization layer between the metallic electrodes and bulk media. Furthermore, there may be a native oxide coating of the metallic electrodes. Both are forming additional capacitances in the system. These capacitances resulting from the electrode design may be larger, preferably much larger than the capacitance of the media or liquid, which should be detected by the sensor. When considering the impedance versus frequency in such an electrode model two cut-off frequencies can be defined, a lower cut-off frequency and an upper cut-off frequency. Thereby a cut-off frequency is regarded as a frequency where the frequency starts going down. Thus, a cut-off frequency in the meaning of the invention is defined as a frequency where the impedance magnitude has changed by plus or minus, preferably 3 dB compared to an adjoining frequency region or substantially constant impedance magnitude versus frequency. Between these cut-off frequencies, the impedance is substantially constant, and in this frequency range the impedance substantially corresponds to the resistance of the media or liquid between the electrodes. The use of a frequency or frequency range near or substantially above the upper cut-off frequency allows to find the capacitance of the media between the electrodes from the impedance measured. Thus, the influence of the capacitance resulting from the electrode material and electrode design can be eliminated.

Said conduit may be a closed circuit, for example a circuit of a cooling system. In an alternative embodiment, the circuit may be an open conduit, for example for the liquid to be pumped.

Preferably, said sensor and said evaluation unit are configured for measurement of a concentration of glycol in said liquid, further preferably of glycol in water. For example, in a sealing system as described above, water may enter the chamber containing a mixture of glycol and water due to wear of a seal. By this, the concentration of glycol in water will change. By detection of the concentration or change in concentration, therefore, wear or a fault of a seal can be detected.

As mentioned above, said sensor preferably comprises at least two electrodes. These electrodes preferably are distanced from one another. The electrodes may be metallic electrodes.

For example, one of said at least two electrodes may form an inner electrode, which is surrounded by the other electrode forming an outer electrode. The outer electrode may contain openings to allow a fluid flow to the inside of the outer electrode to ensure an exchange of liquid or media between the inner and the outer electrode. The outer electrode may have a tubular shape surrounding the inner electrode, which further preferably is centered inside the inner electrode. Preferably, the outer and/or the inner electrode are circular in cross section.

As mentioned before, preferably the sensor comprises at least two electrodes being in contact with said liquid. This means there is no insulating layer between the electrodes, in particular metallic electrodes and the liquid. By such design, an influence of an insulating layer, in particular a capacitance of the insulating layer is eliminated.

According to a preferred embodiment of the invention the used at least one frequency is greater than 250 kHz, further preferably greater than 500 kHz or greater than 1 MHz. This means the evaluation unit is configured such that the measurement can be carried out by use of an electrical signal having such frequency. Preferably the afore-mentioned upper cut-off frequency is a frequency in the range greater than 250 kHz, preferably greater 500 kHz or even 1 MHz as mentioned before. It has been found that with such high frequencies the concentration of the fluid, preferably via the capacitance, can be detected. In particular these frequencies are advantageous for the measurement of a concentration of glycol in a liquid.

According to a preferred embodiment, said evaluation unit comprises a frequency generator generating an electrical signal of variable frequency or a signal comprising a range of frequencies or a white noise-type signal (substantially containing all frequencies). In particular, the frequency generator is configured to generate electrical signals of different frequencies below and above the afore-mentioned upper cut-off frequency. According to a preferred embodiment, the frequency generator is configured such that it can generate frequencies in the range defined in the preceding paragraph. According to a special embodiment of the invention, the frequency generator may be configured to generate a range of frequencies to allow a simultaneous measurement at different frequencies. Alternatively, it would also be possible to provide a frequency generator configured to generate a white noise-type signal. To use a range of frequencies or white noise-type signal (including multitude of different frequencies or substantially all frequencies) the evaluation unit preferably is configured to measure the whole spectral response of impedance signals detected by the sensor simultaneously. On basis of such a response, a spectral analysis may be carried out to detect the response signals at certain frequencies, preferably predefined or selected frequencies.

According to a further embodiment of the invention, said evaluation unit is configured to measure an impedance of the liquid between two sensor electrodes, preferably by use of an electrical signal applied to the electrodes having at least one frequency below said upper cut-off frequency. The respective frequency may be provided by a frequency generator as mentioned before. Furthermore, the sensor electrodes may be configured as described above. The detection of the impedance between the electrodes below the upper cut-off frequency is advantageous because in this frequency range below the upper cut-off frequency and above the lower cut-off frequency, the impedance is substantially constant and is proportional or corresponds to the resistance of the media between the two electrodes. Thus, conductivity can be measured in this middle range of the frequency between the two cut-off frequencies. As defined above the lower cut-off frequency is a frequency where the impedance magnitude changes by 3 dB or more compared to an adjoining frequency region, in particular falling from a plateau of substantially constant impedance magnitude. On basis of the detected impedance or the detected resistance of the media between two electrodes, it is further possible to calculate the capacitance of the medium between the electrodes. On basis of the calculated capacitance, the concentration can be determined.

Preferably, the evaluation unit is configured such that in a first measurement step, said impedance value is detected and in a second measurement step, said detection of said concentration is carried out using the impedance value or resistance value, respectively, which have been detected before. In an alternative solution, the measurement of the impedance or resistance and the detection of the capacitance of the medium between the electrodes may be carried out simultaneously. The consideration of the resistance or impedance of the liquid between the electrodes allows the use of electrodes without insulating cover, as described above.

According to a further embodiment of the invention, said evaluation unit is configured such that for detection of the concentration, said cut-off frequency is detected and a capacitance of the liquid is calculated or determined on basis of said cut-off frequency detected, wherein preferably the capacitance is determined by the following equation:

$$C_m = \frac{1}{2\pi R_m f_2},$$

wherein $C_m$ is the capacitance of the liquid, $R_m$ is the resistance of the liquid and $f_2$ is the upper cut-off frequency. The resistance $R_m$ preferably is measured by use of a frequency below the upper cut-off frequency, i.e. in a frequency range showing a constant impedance and in which the impedance corresponds to the resistance $R_m$. The upper cut-off frequency $f_2$ is detected by measurement of the impedance at at least two frequencies, preferably a multitude of frequencies, at least one below the cut-off frequency and one above the cut-off frequency. From these impedance measurements, the cut-off frequency can be calculated or identified by analysis of the detected impedance. The cut-off frequency $f_2$ for example can be found according to the following equation:

$$f_2 = \frac{\sigma}{2\pi\varepsilon_0\varepsilon_r},$$

wherein $\sigma$ is the conductance of the liquid, $\varepsilon_0$ is the vacuum permeability and $\varepsilon_r$ is the relative dielectric constant of the media, thus showing an absence of any dependency on geometrical sensor properties.

As mentioned before, the conductivity can be measured in the middle range of the frequency below the upper cut-off frequency. With knowledge of the conductivity, $\sigma$ or a resistance $R_m$, it is possible to find the capacitance of the media $C_m$ by measuring the cut-off frequencies.

According to a further embodiment of the invention, said evaluation unit is configured such that a resistance or impedance value and said upper cut-off frequency are detected in a single measurement step, preferably by using an electrical signal having a multi-frequency spectrum and a spectral analysis of the measured impedance frequency response. By this, the complex measurement can be carried out in one step to speed up the measurement procedure. The multi-frequency spectrum may be a spectrum containing several predefined frequencies. In an alternative solution, a white noise type signal (including all frequencies) may be used and a measurement or analysis of the frequency response is carried out at certain predefined frequencies only. This means, the selection of the frequencies to be analyzed can be made either by selecting a frequency of the signal sent or the frequency response analyzed. It would also be possible to select predefined frequencies for both, i.e. sending and analyzing.

According to a further embodiment, said evaluation unit is configured to determine said concentration on basis of the detected capacitance of the liquid, preferably by use of a predefined relation of capacitance and concentration stored in a memory of the evaluation unit. The relation between capacitance and concentration may be determined experimentally and stored in a memory of the evaluation unit.

Since there may be an influence of the temperature, according to a further preferred embodiment it is possible to design the evaluation unit, such that it is connected to a temperature sensor detecting the temperature of the liquid inside the conduit or chamber. Furthermore, the evaluation unit may be configured such that it takes into consideration the temperature value detected by a temperature sensor, when determining the concentration on basis of the detected or calculated capacitance. For this purpose, the temperature influence on the capacitance for different concentrations may also be determined experimentally and stored in the memory of the evaluation unit.

The evaluation unit and the sensor may, according to a further possible embodiment, form a resonator and the evaluation unit may be configured to determine a resonance frequency and to determine the capacity of the liquid on basis of the detected resonance frequency. By this design, it is possible to more accurately find the capacitance. For this, an inductor may be used or connected to the electrodes to form the resonator. The resonance frequency is well-defined and can be found by measuring the frequency, where the phase angle is crossing zero degrees. For a parallel resonator, the resonance frequency $f_0$ may be defined as:

$$f_o = \frac{1}{2\pi\sqrt{LC}},$$

wherein L is the inductance and C is the total capacitance of the resonator. The resonance frequency occurs at a point, where the impedance peaks. Preferably, this resonance frequency is a frequency above the upper cut-off frequency, so that the respective frequency range above the upper cut-off frequency will be analyzed by the evaluation unit to detect the resonance frequency.

Beside the pump device described before, also a method for determining the concentration of a substance in a liquid is subject of the present invention. The method according to the invention in particular may be applied in a pump device, preferably in a pump device described before. It has to be understood that features which were described above with relation to a pump may also be preferred features of the method and features of the method, which are described below, may also be preferred features of the pump device, i.e. that preferred method steps may be implemented into the pump device by respective design of the evaluation unit.

The method according to the invention is provided for determining the concentration of a substance or compound in a liquid, which is contained in a chamber or conduit, preferably of a pump, and further preferably a pump as described above. This in particular may be for example a waste-water pump. According to the method, the concentration is determined on basis of an impedance measurement. This measurement for detecting said concentration is carried out by use of an electrical signal, which may be applied to a sensor, in particular a sensor having at least two electrodes. This electrical signal has at least one frequency corresponding to or above an upper cut-off frequency of a frequency range showing a constant impedance. The upper cut-off frequency is defined above in relation to the pump device according to the invention.

Preferably, the electrical signal has a frequency greater than 250 kHz, further preferably greater than 500 kHz or greater than 1 MHz. These frequencies are preferred in particular for the detection of concentration of glycol in a liquid.

Preferably, the impedance measurement is carried out by use of a sensor having two electrodes in contact with said liquid, wherein said electrical signal is applied to said sensor electrodes. For further advantageous and preferred embodiments of this arrangement, it is referred to the above-mentioned description in connection with the pump device.

The capacitance of the liquid preferably is detected and said concentration is preferably determined on basis of said capacitance, further preferred on basis of a relation of capacitance and concentration determined before. As explained above for the pump device, this relation may be determined experimentally and stored in a memory of an evaluation unit.

According to a further embodiment of the invention, said capacitance of the liquid is detected and said concentration is determined on basis of said capacitance, wherein said capacitance is determined by detecting the resistance of said liquid and said upper cut-off frequency and/or detecting a resonance frequency of a resonator influenced by the capacity of said liquid. By using the resonance frequency, it is possible to detect the capacitance and the concentration more exactly. Also for this feature, it is referred to the foregoing description with reference to a pump device.

Beside the pump device and the method described before, a sensor unit for determining the concentration of the substance inside a liquid is subject of the present invention. The sensor unit preferably is configured to carry out the method mentioned before or to be used inside the pump device as described above. In view of this it has to be understood that the features referring to the sensor and described above with relation to a pump and the method may also be preferred features of the sensor unit, which is described below. The sensor unit according to the invention may be used for detection of a concentration of a substance in a liquid in various solutions or facilities. The sensor unit according to the invention comprises at least one concentration sensor and an evaluation unit connected to said sensor. The sensor is configured such that it can be arranged inside a chamber or conduit containing the liquid to be analyzed. The sensor and the evaluation unit are configured to carry out an electrical impedance measurement to measure or determine the concentration. Said evaluation unit is configured such that a measurement for determining the concentration is carried out by use of an electrical signal which is applied to the sensor. The signal has at least one frequency corresponding to or above an upper cut-off frequency of a frequency range showing a constant electrical impedance. Preferably, the frequency is greater than 250 kHz, further preferably greater than 500 kHz or greater than 1 MHz as discussed above with reference to the pump device and method.

Preferred embodiments of the invention are described by way of example with reference to the accompanying drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
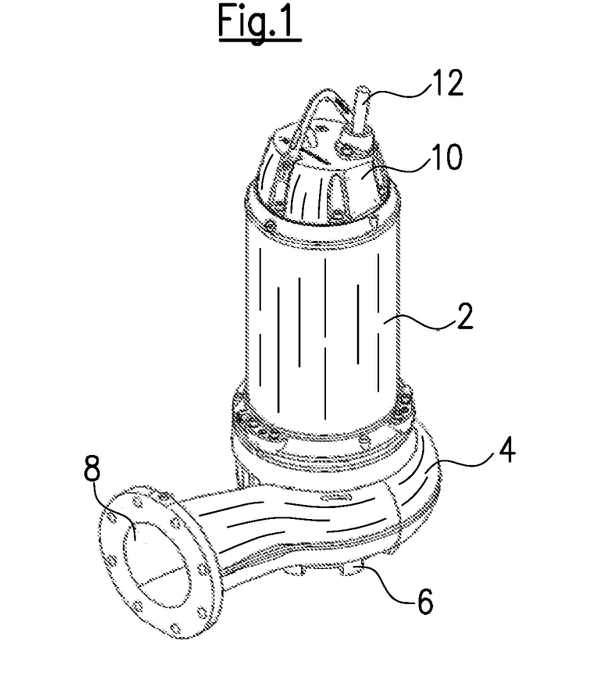
FIG. 1 is a perspective view showing a pump device according to the invention.

The example of a pump device according to the invention shown in FIG. 1 is a submersible waste-water pump. The pump device has a motor housing 2 attached to a pump housing 4. The pump housing 4 contains an impeller, which is driven by an electric drive motor arranged in the motor housing 2. The pump housing 4 has an inlet 6 on the bottom side and an outlet 8 extending in radial direction from the pump housing 4 and configured to be connected with a further outlet pipe. On top of the motor housing 2, there is arranged an electronic housing 10 containing a control electronics for the drive motor. Connected to the electronic housing 10 is a supply cable for the electric power supply 12. Between the motor housing 2 and the pump housing 4, there is arranged a sealing assembly to separate the interior of the motor housing 2 from the pump housing 4, since the motor housing 2 is dry, whereas the interior of the pump housing 4 is filled with a liquid as water to be pumped. The shaft 14 of the drive motor 14 with its free end 16 is connected to an impeller (not shown in FIG. 2). The shaft 14 extends through two shaft seals 18 and 20, which are distanced from one another. Between the two shaft seals and surrounding the shaft 14 is arranged a closed sealing chamber 22 filled with a lubricant or coolant in form of a glycol-water-mixture. The lubricant serves for lubrication of the shaft sealings 18 and 20 and for cooling. Inside the sealing chamber 22, there are arranged two sensors, an impedance sensor 24 and a temperature sensor 26, which are connected to an evaluation unit 28. The evaluation unit 28 may be a separate unit and may be connected to the control electronics arranged in the electronic housing. Alternatively, it would be possible to also arrange the evaluation unit 28 inside the electronics housing 10. The impedance sensor 24 serves as a concentration sensor for detecting the concentration of glycol in the lubricant contained in the sealing chamber 22. By change of the concentration of glycol, in particular, if the concentration decreases, entering of water into the sealing chamber 22 from the interior of the pump housing 4 can be detected. This is an indication for a wear of the shaft sealing, i.e. the first shaft sealing 18 towards the pump housing 4.

Figure 3:
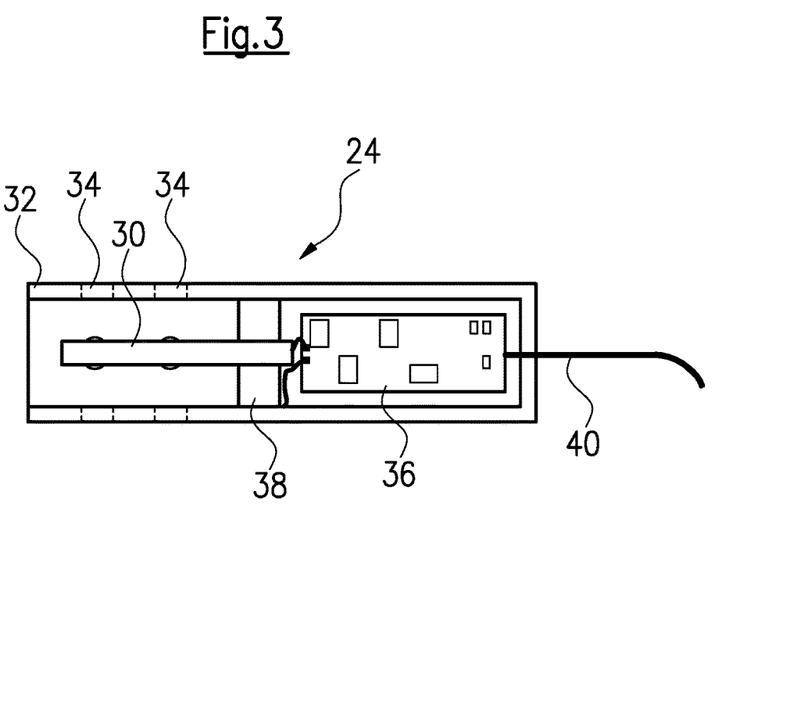
FIG. 3 is a schematical cross-section of an impedance sensor as shown in FIG. 2.
Figure 4:
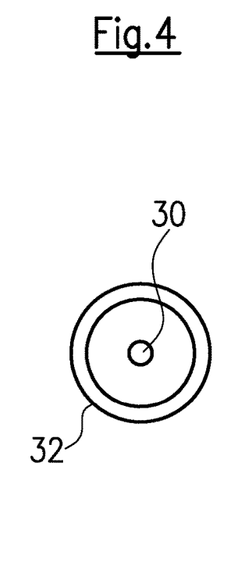
FIG. 4 is a front view of the sensor according to FIG. 3.

The impedance sensor 24 comprises two electrodes 30 and 32, as shown in FIGS. 3 and 4. The electrode 30 forms an inner electrode 30, which is surrounded by an outer electrode 32. The outer electrode 32 has a tubular shape with an open front end. The inner electrode 30 extends in the axial direction of the outer electrode 32 and is arranged centered in the middle of the outer electrode 32, which has a circular cross-section. In the outer electrode 32, there are provided openings allowing an exchange of liquid in the inner space of the outer electrode 32. The electrodes 30 and 32 are connected to sensor electronics 36 arranged in a sealed section inside the outer electrode 32. This sealed section or chamber containing the sensor electronics 36 is separated from the fluid containing area inside the outer electrode 32 by a separating wall 38. The impedance sensor 24 may be connected to the evaluation unit 28 via a sensor cable 40.

Figure 5:
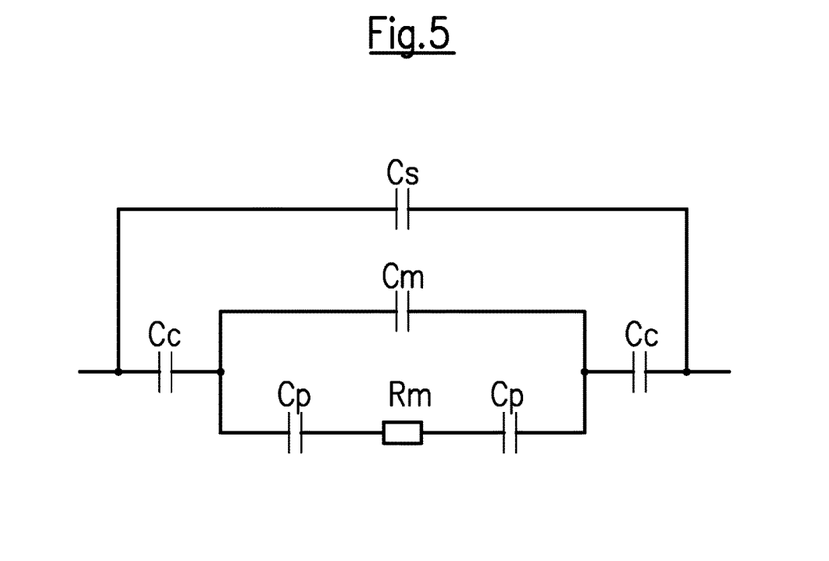
FIG. 5 is a circuit model for the metallic electrode of the sensor according to FIGS. 3 and 4.

The inner electrode 30 and the outer electrode 32 are metallic electrodes, which are in direct contact with the lubricant or coolant inside the sealing chamber 22. This results in the circuit model as shown in FIG. 5. In FIG. 5, the capacitance $C_m$ is the capacitance of the media between the electrodes, i.e. of the lubricant inside the chamber 22. $R_m$ represents the resistance of the media between the electrodes, i.e. the lubricant. $C_p$ represents the capacitance of a polarization layer occurring on the surface of the electrode. Cc represents the capacitance resulting from a native oxide coating of the electrode. $C_s$ is a stray or parasitic capacitance, in particular the stray capacitance of the cable.

For the evaluation of the capacitance of the media $C_m$ it is assumed that the capacitance of the coating and the polarization layer is much larger than the capacitance of the media, which is to be detected. Furthermore, it can be assumed that the stray capacitance $C_s$ is much smaller than the capacitance of the electrode.

Figure 6:
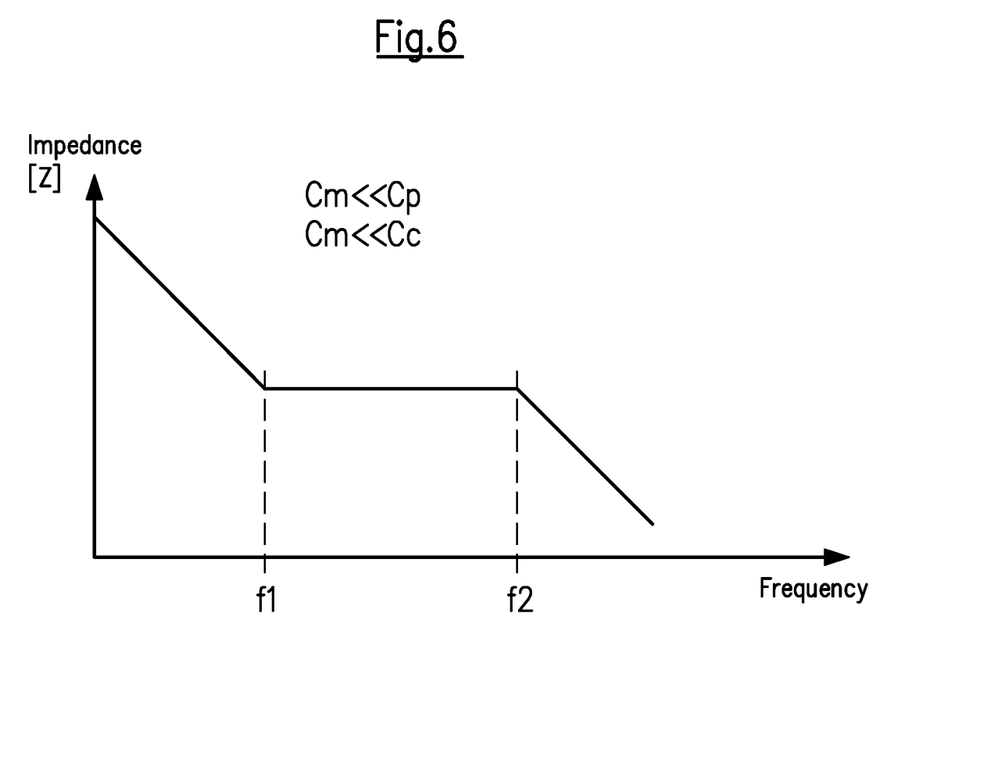
FIG. 6 is a schematic graph view showing y the impedance vs. frequency of the electrode model.

These capacitances and the resistance of the media define two characteristic cut-off frequencies $f_1$ and $f_2$, as shown in FIG. 6. These cut-off frequencies can be calculated according the following equations:

$$f_1 = \frac{1}{2\pi R_m \text{Min}(C_p, C_c)}$$

$$f_2 = \frac{1}{2\pi R_m C_m}$$

For electrodes, which are larger than a few mm$^2$, the capacitances $C_p$ and $C_c$ can be assumed as being much larger than $C_m$. Therefore, the upper cut-off frequency $f_2$ is much larger than the lower cut-off frequency $f_1$. The capacitance of the media, which represents a concentration of glycol inside the lubricant, can be found from the impedance above the upper cut-off frequency $f_2$. This measurement may be difficult due to the low impedance of the electrode. Between the lower cut-off frequency $f_1$ and the upper cut-off frequency $f_2$, the impedance corresponds to the resistance $R_m$ between the two electrodes 30 and 32. Furthermore, the impedance Z is substantially constant in this frequency range. Therefore, it is preferred to measure the resistance $R_m$ of the media in this frequency area, i.e. by applying an electrical signal in the frequency range between the lower cut-off frequency $f_1$ and the upper cut-off frequency $f_2$ to the sensor electrodes 30 and 32. For generating the respective frequency signal, a frequency generator is integrated into the evaluation unit 28. Such a frequency generator may be configured to provide single predefined frequencies or ranges of frequencies, i.e. a spectrum of frequencies allowing a measurement at several frequencies at the same time.

The capacitance of the media of such model would be as following:

$$C_m = \frac{2\pi \varepsilon_0 \varepsilon_r L}{\ln\left(\frac{b}{a}\right)},$$

wherein L is the axial length of the electrode, a is the diameter of the inner electrode 30 and b the diameter of the outer electrode 32. $\sigma$ is the conductance of the media. $\varepsilon_0$ and $\varepsilon_r$ correspond to the vacuum permeability and the relative dielectric constant of the media, i.e. the glycol-water-mixture inside the chamber 22.

The resistance $R_m$ can be calculated as follows:

$$R_m = \frac{\ln\left(\frac{b}{a}\right)}{2\pi L \sigma}$$

From this, it follows that the cut-off frequency $f_2$ could be found independent of the electrode geometry and only depends on the material properties of the media, i.e. the liquid to be analyzed:

$$f_2 = \frac{\sigma}{2\pi \varepsilon_0 \varepsilon_r},$$

since the upper cut-off frequency $f_2$ is much larger than the lower cut-off frequency $f_1$. The conductivity or resistance, respectively, can be measured in the middle range between the lower cut-off frequency $f_1$ and the upper cut-off frequency $f_2$, since in this range the impedance corresponds to the resistance:

$$|Z|=R_m, f_1 < < f < < f_2,$$

wherein Z is the impedance.

With measuring the resistance $R_m$, it is possible to find the capacity of the media by detecting or measuring the upper cut-off frequency $f_2$:

$$C_m = \frac{1}{2\pi R_m f_2}$$

The upper cut-off frequency f2 may be calculated or detected by frequency analysis by measurement of the impedance at several frequencies. This means the cut-off frequency is measured by measuring the impedance at at least two frequencies, one in the area between the two cut-off frequencies, i.e. below the upper cut-off frequency and one above the upper cut-off frequency. Preferably, more than two measurements are carried out and then the uppercut-off frequency is calculated on basis of the measured impedance. In practice, it is preferable that the impedance is measured at a larger number of frequencies, for example 10 to 20 or even more frequencies or a frequency sweep between a lower limit and a higher limit frequency. By this, the upper cut-off frequency and the capacitance $C_m$ of the media can be found with higher accuracy.

Figure 7:
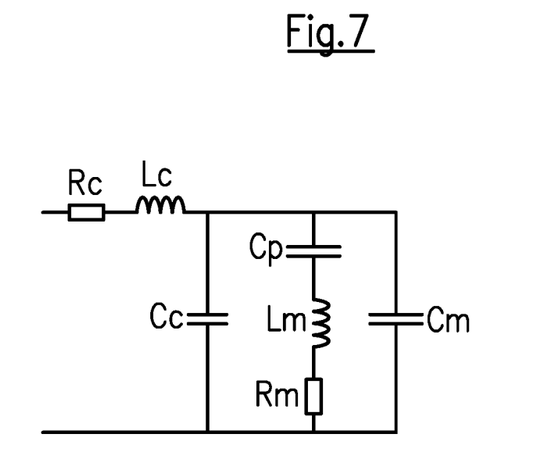
FIG. 7 is a circuit model for the electrode including an inductor to form a resonator.

To further improve the measurement and the detection of the capacity $C_m$ of the media, a resonator can be used. A resonator can be created by introducing a inductor $L_m$ into the electrode circuit, as shown in FIG. 7 showing a model of the electrode additional having an inductor $L_m$. In this model of the electrode $R_c$, $L_c$ and $C_c$ represent the impedance of the cable. $L_m$ is the inductance in the electrode. $C_p$ is the capacitance resulting from a polarization layer, $R_m$ is the resistance of the media and $C_m$ the capacitance of the media to be detected. By using such a resonator, it is possible to find a resonance frequency above the upper cut-off frequency $f_2$. The resonance frequency can be detected by frequency analysis, in particular on basis of the phase angle. Preferably, the capacitance $C_m$ is detected at the resonance frequency.

Figure 2:
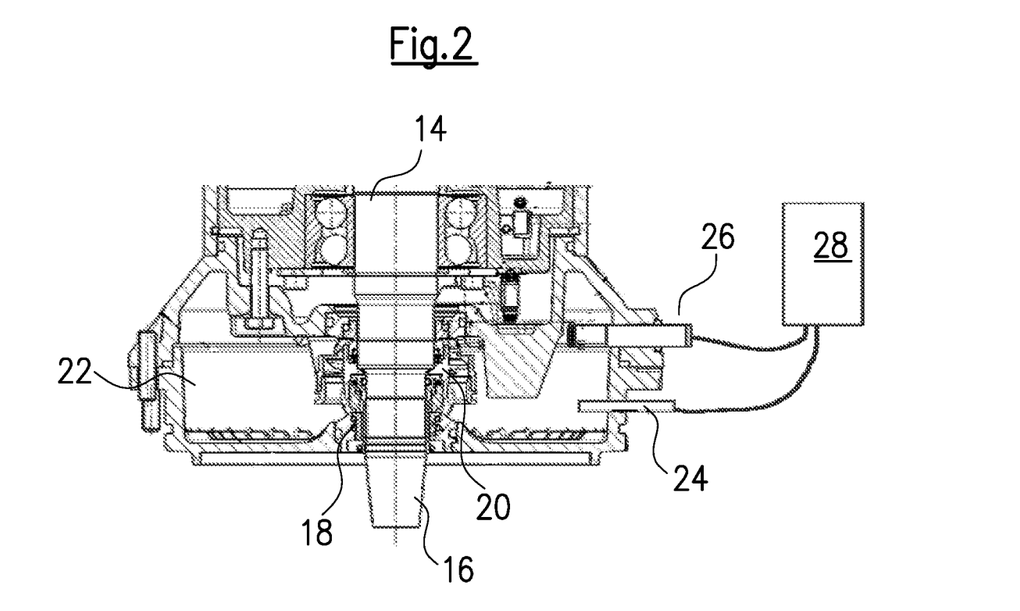
FIG. 2 is a partial cross-sectional view of a sealing chamber of the pump device according to FIG. 1.

On basis of the capacitance $C_m$ of the liquid, the concentration can be detected. The concentration for different capacitances is determined experimentally before the relation may be stored in form of a table inside the evaluation unit 28. Furthermore, the relation may be determined temperature-depending, so that a temperature signal from the temperature sensor 26 detecting the temperature of the media inside the sealing chamber 22 may be considered by the evaluation unit 28. On basis of the temperature signal and the capacitance of the media $C_m$ detected, the evaluation unit 28 determines the corresponding concentration from the stored data. The evaluation unit 28 may have a predefined threshold for an allowable glycol concentration and may give an alarm signal, if the concentration falls below this threshold. The alarm signal is an indication for a fault or wear of the shaft sealing.

While specific embodiments of the invention have been shown and described in detail to illustrate the application of the principles of the invention, it will be understood that the invention may be embodied otherwise without departing from such principles.

LIST OF REFERENCE NUMERALS 2 water housing
4 pump housing
6 inlet
8 outlet
10 electronic housing
12 supply cable
14 shaft
16 free end
18, 20 shaft sealings
22 sealing chamber
24 impedance sensor
26 temperature sensor
28 evaluation unit
30 inner electrode
32 outer electrode
34 opening
36 sensor electronics
38 separating wall
40 sensor cable

The invention claimed is:
1. A pump device comprising:
at least one chamber or conduit containing or provided for containing a liquid;
a concentration sensor arranged in said chamber or conduit for detecting a concentration of a substance in said liquid; and
an evaluation unit connected to said sensor, wherein said sensor and said evaluation unit are configured for an electrical impedance measurement, and said evaluation unit is configured such that a measurement for detecting said concentration is carried out by use of an electrical signal applied to said sensor having at least one frequency corresponding to or above an upper cut-off frequency of a frequency range showing a constant electrical impedance, wherein a capacitance of said liquid is detected and said concentration is determined based on said capacitance, wherein said capacitance is determined by detecting a resistance of said liquid and said upper cut-off frequency and/or detecting a resonance frequency of a resonator influenced by a capacity of said liquid.
2. A pump device according to claim 1, wherein said chamber or circuit is part of a sealing system.
3. A pump device according to claim 2, wherein said circuit is a closed circuit.
4. A pump device according to claim 1, wherein said conduit is part of a flow path for a liquid to be pumped.
5. A pump device according to claim 1, wherein said sensor and said evaluation unit are configured for measurement of a concentration of glycol in said liquid.
6. A pump device according to claim 1, wherein said sensor comprises two electrodes which are distanced from one another.
7. A pump device according to claim 6, wherein one of said two electrodes forms an inner electrode which is surrounded by the other electrode forming an outer electrode.
8. A pump device according to claim 1, wherein the sensor comprises two electrodes being in contact with said liquid.
9. A pump device according to claim 1, wherein said evaluation unit is configured such that the at least one frequency is greater than 250 kHz.
10. A pump device according to claim 1, wherein said evaluation unit comprises a frequency generator generating an electrical signal of variable frequency or a signal comprising a range of frequencies or a white noise signal.
11. A pump device according to claim 1, wherein said evaluation unit is configured to measure an impedance of the liquid between two sensor electrodes of the sensor by use of an electrical signal applied to the electrodes having at least one frequency below said upper cut-off frequency.
12. A pump device according to claim 10, wherein said evaluation unit is configured such that in a first measurement step said impedance value is detected and in a second measurement step said detection of said concentration is carried out using the impedance value detected before.
13. A pump device according to claim 1, wherein said evaluation unit is configured such that for detection of the concentration said cut-off frequency is detected and said capacitance of the liquid is calculated on basis of said cut-off frequency detected, wherein preferably the capacitance is determined by following equation:

$$C_m = \frac{1}{2\pi R_m f_2}$$

wherein $C_m$ is the capacitance of the liquid, $R_m$ is the resistance of the liquid and $f_2$ is the upper cut-off frequency.
14. A pump device according to claim 1, wherein said evaluation unit is configured such that a resistance or impedance value and said upper cut-off frequency are detected in a single measurement step, by using an electrical signal having a multi-frequency spectrum and a spectral analysis of the measured impedance frequency response.
15. A pump device according to claim 1, wherein the evaluation unit is configured to determine said concentration on basis of the detected capacitance of the liquid, by use of a predefined relation of capacitance and concentration stored in a memory of the evaluation unit.
16. A pump device according to claim 1, wherein the evaluation unit and the sensor form a resonator and the evaluation unit is configured to determine a resonance frequency and to determine the capacity of the liquid on basis of the detected resonance frequency.
17. A method for determining the concentration of a substance in a liquid contained in a chamber or conduit, the method comprising
determining the concentration on basis of an impedance measurement; and
measuring for detecting said concentration by use of an electrical signal having at least one frequency corresponding to or above an upper cut-off frequency of a frequency range showing a constant impedance, wherein a capacitance of the liquid is detected and said concentration is determined based on said capacitance, wherein said capacitance is determined by detecting the resistance of said liquid and said upper cut-off frequency and/or detecting a resonance frequency of a resonator influenced by a capacity of said liquid.

18. A method according to claim 17, wherein said impedance measurement is carried out by use of a sensor having two electrodes in contact with said liquid, wherein said electrical signal is applied to said sensor electrodes.

19. A method according to claim 17, wherein the capacitance of the liquid is detected and said concentration is determined on basis of said capacitance, on basis of a relation of capacitance and concentration determined before.

20. A sensor unit comprising:
a sensor provided for arrangement inside a conduit or space containing a liquid; and
an evaluation unit connected to said sensor, wherein said sensor and said evaluation unit are configured for detecting a concentration of a substance in a liquid by an electrical impedance measurement, wherein said evaluation unit is configured such that a measurement for detecting said concentration is carried out by use of an electrical signal applied to said sensor having at least one frequency corresponding to or above an upper cut-off frequency of a frequency range showing a constant electrical impedance, wherein a capacitance of said liquid is detected and said concentration is determined based on said capacitance, wherein said capacitance is determined by detecting a resistance of said liquid and said upper cut-off frequency and/or detecting a resonance frequency of a resonator influenced by a capacity of said liquid.

21. A pump device according to claim 1, wherein said capacitance is based on a change in a dielectric constant of said liquid.

\* \* \* \* \*